United States Patent [19]
West et al.

[11] Patent Number: 5,550,148
[45] Date of Patent: Aug. 27, 1996

[54] PAF SYNTHESIS MODULATORS

[75] Inventors: Robert R. West, Seattle; Jeffrey Van Ness, Bothell, both of Wash.; Annemarie R. Varming, Charlottenlund, Denmark

[73] Assignees: ZymoGenetics, Inc., Seattle, Wash.; Novo Nordisk A/S, Bagsvaerd, Denmark

[21] Appl. No.: 482,248

[22] Filed: Jun. 7, 1995

[51] Int. Cl.⁶ .................. A61K 31/40; C07D 207/22
[52] U.S. Cl. ...................... 514/408; 548/532; 548/518
[58] Field of Search .................... 548/539; 514/423

[56] References Cited

FOREIGN PATENT DOCUMENTS 2275926  9/1994  United Kingdom .

OTHER PUBLICATIONS

Chao et al., *Biochem. J.* 292:617–629, 1993.
Sawa et al., *J. Antibiotics* 45(1):136–139, 1992.
Hayakawa et al., *Tetrahedron Letters* 32(2):213–216, 1991.
Henderson, *J. Allergy Clin. Immunol.* 79(4):543–553, 1987.
Venable et al., *J. Lipid Res.* 34:691–702, 1993.
Braquet et al., *Pharmacological Reviews* 39(2):97–145, 1987.

*Primary Examiner*—Johann Richter
*Assistant Examiner*—Ebenezer Sackey
*Attorney, Agent, or Firm*—Debra K. Leith; Gary E. Parker; Deborah A. Sawislak

[57] ABSTRACT

Compounds that selectively modulate the remodeling pathway of platelet activating factor (PAF) are described. Related pharmaceutical compositions and methods are also disclosed. These compounds, pharmaceutical compositions and methods are useful for reducing or eliminating inflammation.

8 Claims, No Drawings

PAF SYNTHESIS MODULATORS

DESCRIPTION

1. Technical Field

The present invention is directed to compounds that selectively modulate the remodeling pathway of platelet activating factor (PAF) synthesis, as well as related pharmaceutical compositions and methods. These PAF synthesis modulators are useful as anti-inflammatory agents.

2. Background of the Invention

Inflammation is characterized by redness, swelling, heat and pain. These symptoms result from capillary dilation, leading to accumulation of fluid (edema) and migration of phagocytic leukocytes. Inflammatory states may be acute or chronic. For a general review of inflammation, see Fundamental Immunology, 3rd Edition, W. E. Paul (ed.), Raven Press, New York, N.Y., 1993, Chapter 29.

Inflammation plays a critical role in elimination of foreign substances. Generally, recognition components of the host's immune system bind to epitopes of the foreign matter, activating an amplification system that includes the complement cascade, cytokines, the coagulation cascade, lipid mediators and amines produced by mast cells. These activated systems and components alter blood flow, increase vascular permeability, augment adherence of circulating leukocytes to vascular endothelium, promote migration of leukocytes into tissues, and stimulate leukocytes to destroy the foreign substance. If the foreign matter is not eliminated by mononuclear phagocytes, such elimination occurs in tissue spaces and is performed by polymorphonuclear leukocytes (neutrophils and eosinophils), monocytes or cytotoxic lymphocytes that are recruited from the blood.

Elimination of foreign antigens does not generally produce clinically apparent inflammation. A clinical inflammatory state may occur if a large amount of foreign matter is present, if the antigen is present in an unusual location, or if the antigen is difficult to digest. Inflammation may also be a symptom of certain diseases, such as rheumatoid arthritis, autoimmune diseases, or acquired immunoregulatory abnormalities.

Platelet activating factor (PAF) is a phospholipid mediator of the above-noted antigen elimination/ inflammatory process. Platelets produce a group of platelet-activating factors (PAFs) that are acetyl-alkylglycerol ether analogs of phosphatidylcholine. These PAFs cause platelet aggregation, phagocyte chemoattraction, stimulation of lysosomal enzyme release, and reactive oxygen product formation by neutrophils, eosinophils and macrophages. Leukocytes can also produce PAFs in response to inflammatory mediators, leading to increased vasopermeability, vasodilation and bronchoconstriction. In normal circumstances, PAF is an effective bioactive mediator of a host's response to routine physiological stimuli, such as destruction of foreign substances. However, in certain situations and diseases, PAFs may lead to pathologies (such as ischemia-reperfusion, necrotizing enterocolitis and asthma) when a response to a foreign body or self-antigen is turned upon the host itself. In the latter instance, an elevated concentration of PAF can initiate tissue injury associated with inflammation. Bazan provides a concise summary of PAF and its role in inflammation in *Nature* 374:501–02, 1995.

Accordingly, there is a need in the art for compounds that have anti-inflammatory activity. In addition, there is a need for active agents useful as lead compounds in drug development, and in particular for development of anti-inflammatory drugs, including drugs that selectively modulate the remodeling pathway of PAF synthesis.

SUMMARY OF THE INVENTION

It is an object of the present invention to provide compounds of known identity and structure. These compounds selectively modulate the remodeling pathway of platelet activating factor synthesis, and are useful as anti-inflammatory agents.

It is a further object of the present invention to provide pharmaceutical compositions comprising the claimed compounds in combination with a pharmaceutically acceptable vehicle.

It is yet another object of the present invention to provide methods for reducing inflammation in a mammal comprising administering a therapeutically effective amount of the claimed pharmaceutical compositions.

It is another object of the present invention to provide methods for producing the claimed compounds.

Within one aspect of the invention, the claimed compounds are administered in combination with one or more anti-inflammatory agents.

Within another aspect of the invention, the claimed compounds are administered to a mammal suffering from or experiencing septic shock, anaphylaxis, thrombosis, adult respiratory syndrome, ischemia-reperfusion, necrotizing enterocolitis, asthma, rheumatoid arthritis, an autoimmune disease or an acquired immunoregulatory abnormality.

Within yet another aspect of the invention, a culture that makes the claimed compounds is extracted with an organic solvent prior to recovery of the claimed compounds.

These and other aspects of the invention will become evident upon reference to the following detailed description.

DETAILED DESCRIPTION OF THE INVENTION

A modulator of the remodeling pathway of platelet-activating factor (PAF) synthesis, designated 1494, was originally identified by a high throughput screen of natural product extracts. Compound 1494 of the present invention is produced by aerobic fermentation of fungal culture ZG1494, originally isolated from red pepper in Denmark. The culture was taxonomically characterized as *Penicillium rubrum* at Centraalbureau voor Schimmelcultures, Oosterstraat 1, 3742 SK Baarn, The Netherlands. This fungus is maintained in the Culture and Metabolites Collection of Novo Nordisk A/S, Novo Alle, 2880 Bagsvaerd, Denmark as culture number NN005289/A03191. A viable culture of this microorganism was deposited with the Centraalbureau voor Schimmelcultures, Oosterstraat 1, 3742 SK Vaarn, The Netherlands on Mar. 28, 1995. It has been deposited under the Budapest Treaty and assigned the strain designation CBS 238.95 by such depository.

A structurally similar compound of the present invention, designated 2158, is produced by aerobic fermentation of fungal culture MO2158, originally isolated from pine root. The culture was taxonomically characterized as *Sclerophoma pythiophila* at Centraalbureau voor Schimmelcultures, Oosterstraat 1, 3742 SK Baarn, The Netherlands. This fungus maintained in the Culture and Metabolites Collection of Novo Nordisk A/S, Novo Alle, 2880 Bagsvaerd, Denmark as culture number NN006262/N0070. A viable culture of this microorganism was deposited with the Centraalbureau voor Schimmelcultures, Oosterstraat 1, 3742 SK Vaarn, The Netherlands in 1995. It has been deposited under the Budapest Treaty and assigned the strain designation CBS 328.95 by such depository.

A compound identical to 2158, designated 1270, is produced by aerobic fermentation of fungal culture MO1270, originally isolated from pine root. The culture was taxonomically characterized as *Sclerophoma species* at Centraalbureau voor Schimmelcultures, Oosterstraat 1, 3742 SK Baarn, The Netherlands. This fungus is maintained in the Culture and Metabolites Collection of Novo Nordisk A/S, Novo Alle, 2880 Bagsvaerd, Denmark as culture number NN006251/N0002. A viable culture of this microorganism was deposited with the Centraalbureau voor Schimmelcultures, Oosterstraat 1, 3742 SK Vaarn, The Netherlands in 1995. It has been deposited under the Budapest Treaty and assigned the strain designation CBS 329.95 by such depository.

Platelet-activating factor, also known as acetylglyceryl ether phosphocholine (AGEPC), 1-o-alkyl-2-sn-acetyl-3-glycero-phosphocholine (alkylacetyl-GPC), alkylacetylglycerophosphocholine (alkylacetyl-GPC) and PAF-acether (hereinafter referred to as PAF), is an especially important target for modulator screening. PAF is a potent phosphocholine-containing glycerolipid involved in a range of normal and pathophysiological responses wherein PAF acts as a vasoactive mediator. PAF is produced by a wide variety of cells and tissues, including hematopoietic cells (e.g., platelets, macrophages and polymorphonuclear cells), epithelial cells (e.g., lung tissue, uterus and kidney) and endothelial cells. PAF acts via binding to cellular PAF receptors as an agonist stimulating a wide range of biological responses, including aggregation and degranulation of platelets and neutrophils, stimulation of chemotaxis, stimulation of chemokinesis, stimulation of superoxide formation, stimulation of protein phosphorylation, stimulation of production of arachidonate and phosphoinositide metabolites, activation of protein kinase C, glyconeogenesis and stimulation of tumor necrosis factor production. The various pathways of signal transduction involving PAF have been adequately reviewed by Chao and Olsen (*Biochem. J.* 292:617–29, 1993). The diverse actions of PAF have been further reviewed by Venable and Prescott (Venable et al., *J. Lipid Res.* 34:691–702, 1993; Prescott et al., *J. Biol. Chem.* 265:17381–84, 1990).

PAF is highly toxic in excess (greater than 1 picomolar), and has been shown to be toxic when administered exogenously. PAF has been implicated in the pathophysiology of a number of clinical inflammatory states, such as septic shock, anaphylaxis, thrombosis and adult respiratory distress syndrome. PAF also possesses normal physiological functions. For example, PAF has potent hypertensive properties that have led to its implication in the physiological regulation of blood pressure (Wykle et al., *J. Biol. Chem.* 255:10256–60, 1980).

Importantly, the pathway for synthesis of PAF involved in normal physiological functions differs from the pathway of PAF synthesis in response to inflammatory stimuli (Billah et al., *J. Biol. Chem.* 261:5824–31, 1986; Prescott, supra). These two routes of PAF synthesis involved in normal and pathophysiological responses are respectively termed the de novo and the remodeling pathways.

Through the constitutive, de novo synthesis pathway, PAF is synthesized from an analog of lysophosphatidic acid, and requires a reaction sequence of acetylation, dephosphorylation and phosphocholine addition steps (see Prescott, supra). The PAF remodeling pathway (also known as the de-acylation-acetylation pathway) is a response-stimulated pathway that involves the structural remodeling of 1-o-alkyl-2-acyl-3-glycerophosphocholine (a phospholipid membrane storage precursor to lyso-platelet activating factor (hereinafter, lyso-PAF)) by the replacement of the acyl group (arachidonic acid) at the 2-position with acetate. Synthesis of PAF via this pathway during hypersensitivity and pathophysiological functions of PAF are generally considered to be mediated via an inflammatory stimulus which triggers initiation of an inflammatory cascade involving activation of the remodeling pathway of PAF synthesis (Venable, *J. Biol. Chem.* 268:7965–75, 1993).

Pathophysiological activities of PAF have made this lipophilic compound the target of recent efforts to identify PAF inhibitors. A number of PAF receptor antagonists have been identified (see Braquet et al., *Pharmacol. Rev.* 39:98–133, 1987). However, the combination of the intracellular activation (autocrine modality) of PAF synthesis and the transient nature of intercellular activation of PAF synthesis generally prevents therapeutic utility of PAF receptor antagonists, which work best with exocrine ligand pairs. More importantly, PAF receptor antagonists may inhibit the normal, necessary physiological functions of PAF, along with any pathophysiological activity.

A number of PAF synthesis inhibitors have also been disclosed by, for example, Hogaboam et al. (*Eur. J. Pharmacol.* 216:315–18, 1992) and Joly et al. (*Eur. J. Pharmacol.* 144:133, 1987). However, the PAF synthesis inhibitors discovered to date have low potency and often inhibit synthesis of a number of physiologically important molecules besides PAF, leading to high toxicity.

The most appropriate targets for therapeutically useful modulators of PAF metabolism are compounds capable of inhibiting PAF synthesis selectively through the remodeling pathway. Such compounds should be useful for inhibiting the pathophysiological functions of PAF in, for example, clinical inflammatory states and respiratory distress syndrome.

The present invention discloses a novel PAF modulator designated as 1494. Compound 1494 was identified using a high throughput screening assay, as described in pending patent application U.S. Ser. No. 08/203,993, filed Feb. 28, 1994. Briefly, the high throughput screening assay is based on the enzymatic activity responsible for mobilization of the membrane storage precursor of lyso-PAF, 1-o-alkyl-2-acyl-3-glycerolphosphocholine (alkylacyl-GPC). While not wishing to be bound by theory, it is currently believed that the acyl group in the 2-position of the glycerol backbone of the phospholipid in PAF is arachidonate, which is a precursor for the eicosanoids. It is commonly believed that phospholipase $A_2$ (PLA2) is responsible for liberating "free" arachidonic acid from alkylacylphosphocholines (or alkylacylethanolamines), which then enter the lipoxygenase or cyclooxygenase pathways. Cleavage of alkylacylglycerophospholipids was believed to generate free arachidonic acid and a lysophospholipid, such as lyso-PAF (reviewed by Glaser et al., *TIBS* 14: 92–98, 1993). Recent work on transacylases (e.g., Uemura et al., *J. Biol. Chem.* 266:8268–72, 1991; Venable et al., *J. Biol. Chem.* 266:18691–98, 1991; Nieto et al., *J. Biol. Chem.* 266:18699–706, 1991) suggests a means for coupling PAF and eicosanoid production. As noted above, however, the exact enzyme target need not be unambiguously identified in order to practice the assay methods of the present invention.

A first screening assay provides a means to detect modulators of the activity of the transacylase (or PLA2) involved in the remodeling pathway of PAF synthesis. Within this assay only an "activity" is being measured; an activity that reflects either a PLA2 enzyme that cleaves arachidonic acid from the sn2 position of alkylacyl-GPC, or a transacylase that remodels alkylacyl-GPC, generating lyso-PAF in the process. This assay thus permits the identification of a putative modulator of the transacylase activity which would modulate both the synthesis of PAF (by modulating the generation of the PAF substrate lyso-PAF) and the availability of arachidonic acid for eicosanoid synthesis.

A second screening assay detects modulators of the formation of PAF from lyso-PAF and acetyl-CoA by an enzyme termed PAF acetyltransferase. This is the second step in the remodeling pathway of PAF synthesis, described by Wykle, J. Biol. Chem. 255:10256–60, 1980.

To aid in the identification of selective modulators, two secondary screens use as targeted enzymes a phosphocholinetransferase (the enzyme responsible for the last step in the de novo pathway; Woodard et al., J. Biol. Chem. 262:2520–27, 1987), and the de novo route acetyltransferase (Lee et al., J. Biol. Chem. 261:5373–77, 1986). Employment of these secondary screens allows identification of modulators, enabling an ordinarily skilled artisan to pinpoint modulators selective for the remodeling pathway of PAF synthesis.

An additional assay is based on an indirect measurement of lyso-PAF synthesis. The assay detects modulators of the conversion of 1-O-alkyl-2-arachidonyl- 3-glycerophosphocholine to lyso-PAF. This assay is conveniently carried out in a 96-well plate format, using plates having well volumes up to 200 µl. The assay is particularly useful for high throughput screening procedures.

To conduct the assay, three parallel samples are run: A test sample, a first control sample, and a second control sample. In each sample, hematopoietic, endothelial or epithelial cells are incubated in the presence of a calcium ionophore to activate the cells. Preferred cells are those of stable transformed cell lines maintained using conventional tissue culture techniques, and include the hematopoietic cell lines HL-60 (ATCC CCL 240), IC-21 (ATCC TIB 186) and SKW 6.4 (ATCC TIB 215); the endothelial cell line HUV-ec-c (ATCC CRL- 1730); and the epithelial cell line BUD-8 (ATCC CRL- 1554). Suitable calcium ionophores include the antibiotic A23187, also known as calcimycin (available from Calbiochem, San Diego, Calif.), and derivatives thereof. While not wishing to be bound by theory, the activation is believed to at least partially involve the release of arachidonic acid from 1-O-alkyl-2-arachidonate-3-glycerophosphocholine due to the activation of PLA2 or transacylase enzymatic activity. After a brief incubation period (typically about 1–10 min at 4° C. to 37° C.), the cells are permeabilized according to conventional methods, such as with a 0.1 to 0.5% V/V solution of a non-ionic detergent. Preferred detergents include polyoxyethylenesorbitan monolaurate (TWEEN®-20; available from Pierce, Rockford, Ill.) and the like.

After the cells are activated and permeabilized, a test substance is added to the test sample. The test substance will be any substance to be screened for modulatory activity. Typically, the test substance will be a known compound, such as a component of a chemical library; or an unknown compound, such as a cell extract, medium sample, partially purified fraction of biological origin or the like. The test sample is dissolved or suspended in a 50–100% solution of DMSO, and a small volume (about 1 to 5 µl) of the mixture is added to each of the test samples.

Lyso-PAF (commercially available from, for example, Calbiochem, La Jolla, Calif.) is added to each of the second control samples to a final concentration of 10–20 µM, typically using a stock solution of 10–200 mM in 100% methanol.

Labeled acetyl-CoA is then added to the first control samples, second control samples and test samples. Tritiated acetyl-CoA is preferred. In a typical assay, tritiated acetyl-CoA is added to a final concentration of 1–10 mCi/ml. In addition, unlabeled acetyl CoA is generally added to a concentration of about 10–200 µM.

The solutions are gently mixed for 30–60 sec and incubated at 18° C. to 42° C., preferably about 37° C., for 10–60 min. The samples are then exposed to a solid-phase, lipophilic extraction medium to separate newly synthesized PAF, if present, from labeled acetyl-CoA. Within the 96-well plate format it is preferred to add the extraction medium directly to the wells. Typically, 1–5 mg of extraction medium (e.g., AMBERCHROM CG-71 resin; Supelco, Bellefonte, Pa.) in 10–50 µl of distilled water is added to each well of the plate. The plate is shaken gently for about 1 min, following which the resin is collected. It is convenient to collect the resin on a glass-fiber filter using commercially available harvesting equipment (e.g., 96-well microtiter plate format MICRO-CELL HARVESTER available from Skatron, Waltham, Mass.). The collected resin is washed to remove unincorporated labeled acetyl-CoA, and the labeled acetate incorporated into the separated PAF in each sample is determined. When collecting the resin on filters, the filters are dried (e.g., in a microwave oven for 5–10 min) and counted using conventional scintillation agents and detection equipment.

Percentage inhibition of PAF synthesis is determined by dividing the average of 2 or 3 replicate wells of the test sample by the average of 3 wells of the first control sample and multiplying by 100. Significantly lower incorporation of label in the test sample, as compared to the first control sample, indicates the presence in the test sample of an inhibitor of PAF synthesis. Incorporation of label in the test and second control samples is then compared to determine the presence in the test sample of a specific modulator of the conversion of 1-O-alkyl-2-arachidonyl-3-glycerophosphocholine to lyso-PAF. Inhibition in the test sample of at least 50% of the activity level estimated for the control sample is indicative of an inhibitor in the test sample. Inhibition of 80% or more is preferred.

Compounds 2158 and 1270 were identified using a GLP-1 SPA binding assay. Briefly, membranes from a Cell line expressing recombinant human glucagon-like peptide 1 (GLP-1) receptor were affixed to scintillation proximity assay (SPA) beads (Amersham, Arlington Heights, Ill.). These SPA beads permit detection of radiolabel in proximity to the bead. The GLP-1 receptor beads are combined with a test sample, then combined with radiolabeled (i.e, $^{125}$I-labeled) GLP-1 ligand, and assayed for radiolabel/scintillation. Using SPA technology, it is not necessary to separate bound and free radiolabeled GLP-1. Inhibitors of GLP-1 were detected by a decrease in measured scintillation associated with the beads, as compared to diluent controls.

The discoveries of the present invention are a result of screening large numbers of samples (that could include, for instance; microbial culture extracts, plant extracts, marine extracts, pure chemical compounds, peptides, and combinatorial libraries) using one or more assay systems that permit rapid identification of substances that modulate synthesis or activity of components of the remodelling pathway of PAF synthesis. Secondary screens may be used to identify and eliminate de novo PAF synthesis pathway modulators.

Elucidating the structure of PAF inhibitors of the present invention can be accomplished by conventional methods, well known in the art which may include melting point, molecular weight determination, specific rotation, ultraviolet and infrared absorption spectroscopy, nuclear magnetic resonance (NMR), and mass spectrometry (MS).

Biologically active PAF inhibitors of the present invention are therefore contemplated to be advantageous for use in therapeutic applications for which inhibition of the vasoactive mediator PAF is useful. Such applications where PAF inhibitors of the present invention may be used, for example, are in the treatment of a variety of clinical inflammatory states, including septic shock, anaphylaxis, thrombosis and adult respiratory distress syndrome.

PAF inhibitors of the present invention can be formulated with a pharmaceutically acceptable carrier for parenteral, oral, nasal, rectal, or transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. One skilled in the art may formulate the compounds of the present invention in an appropriate manner, and in accordance with accepted practices, such as those disclosed in *Remington's Pharmaceutical Sciences*, Gennaro (ed.), Mack Publishing Co., Easton, Pa. 1990 (which is incorporated herein by reference in its entirety). The claimed compounds may also be administered in the form of liposomes or sustained release formulations, or by means of implantable pumps or implantable slow release devices, to achieve a consistent dosage over an extended period of time.

The PAF inhibitors of the present invention may be administered alone or in combination with one or more anti-inflammatory compounds known in the art. These known anti-inflammatory compounds include, for instance, steroidal anti-inflammatory drugs and non-steroidal anti-inflammatory drugs.

Pharmaceutical compositions of the present invention are administered in unit dosage form at daily to weekly intervals, in single or multiple doses, or by continuous infusion. An "effective amount" of such a pharmaceutical composition is an amount that provides clinically significant amelioration of a clinical inflammatory state or of a hypo- or hypertensive state. Such amounts will depend, in part, on the particular condition to be treated, age, weight, and general health of the patient, and other factors evident to those skilled in the art. Determination of dose is within the level of ordinary skill in the art. For instance, data from acceped animal models are generally predictive of doses in humans to within one order of magnitude. The rat paw edema model (see, for example, M. Goldenberg and R. Meurer, *Prostaglandins* 28:271–78, 1984) is an exemplary animal model in this regard. Therapeutic doses for the treatment of inflammation in humans can range from about 1 μg to about 100 mg PAF inhibitor per kg body weight of recipient per day. In some instances, after reduction or elimination of an acute inflammatory state, a lower dosage level may be administered to maintain the desired anti-inflammatory effect.

The invention is further illustrated by the following non-limiting examples.

EXAMPLES

Example 1

Isolation and Characterization of 1494A

A. Fermentation Procedure:

Three ml of a spore/mycelium suspension of ZG1494 were used to inoculate a 250 ml baffled shake flask (Wheaton, Millville, N.J.) containing 100 ml of CYA medium (sucrose, 30 g/l; yeast extract (Difco, Detroit, Mich.), 5 g/l; $NaNO_3$, 3.0 g/l; $KH_2PO_4$, 1.0 g/l; $MgSO_4 \cdot 7 H_2O$, 0.5 g/l; KCl, 0.5 g/l; $FeSO_4 \cdot 7 H_2O$ at 1%, 1.0 ml/l; Pluronic at 100%, 0.1 ml/l). The flasks were incubated for 12 d at 26° C. at 200 RPM rotation. Alternatively, ZG1494 was cultured in a one liter fermentation using CYA medium.

B. Extraction Procedure:

The entire culture (medium plus cells) was adjusted to pH 9.0. The culture was then combined with ethyl acetate in a 1:1 ratio and vigorously stirred for 16–18 h at room temperature. The ethyl acetate/broth mixture was centrifuged at 1500 g for 10 min, the organic layer was removed by aspiration and evaporated to dryness using a rotary evaporator under low heat (30° C.). The dried organic material was dissolved into 100 ml of acetonitrile, and then partitioned with 100 ml of hexane in a 250 ml separatory funnel. The hexane layer was removed, and the acetonitrile fraction was repartitioned with 100 ml hexane. The acetonitrile layer was filtered through a sintered glass funnel, and then evaporated to dryness using a rotary evaporator under low heat, yielding 566 mg of dried organic material.

C. Instrumentation:

Preparative HPLC was carried out on a Rainin Dynamax system (Rainin Instrument Co. Inc., Emeryville, Calif.). A Rainin UV-D II dual wavelength detector set at 220 and 270 nm was used to monitor the chromatography, and fractions were collected with a Rainin Dynamax FC-2 fraction collector. Analytical HPLC was carried out on a HP1090 liquid chromatograph (Hewlett Packard, Wilmington, Del.) run with the HP ChemStation (Pascal series) software.

UV spectra were recorded on a DU 640 spectrophotometer (Beckman, Fullerton, Calif.). IR spectra were recorded on a Perkin Elmer 1600 FTIR series detector.

The structure of 1494A was determined by a combination of one and two-dimensional NMR experiments in conjunction with data provided by mass spectrometry. In addition to $^1$H-NMR, $^{13}$C-NMR, double quantum phase sensitive COSY, DEPT, HETCOR, and HMBC experiments, a phase sensitive INADEQUATE experiment was run on this compound at natural abundance to eliminate any ambiguity in the structure assignment.

Mass spectral analysis was performed on a VG-70 SEQ Tandem Hybrid (EBqQ) magnetic sector mass spectrometer (VG Analytical, Manchester, U.K.), and run in the fast atom bombardment mode (FAB). High resolution mass spectrometry was accomplished using PEG 300 for exact mass calibration.

NMR spectra were run on a Varian Unity-Plus 500 MHz or a Bruker AM-500 MHz at a sample concentration of 12 mg in 650 μl of DMSO-$d_6$. The structure was determined using a combination of one and two dimensional NMR experiments in conjunction with the mass spectral data. A one dimensional $^1$H-NMR, a HETCOR (Heteronuclear Correlation; Bax and Morris, *J. Magn. Reson.* 42:501, 1981), a DQFCOSY (phase sensitive-double-quantum filtered COSY; Piatini et al., *J. Am. Chem. Soc.* 104:6800–01, 1982; Rance et al., *Biochem. Biophys. Res. Comm.* 117:479–85, 1983), and an HMBC (inverse detected multiple bond correlation; Bax and Summers, *J. Am. Chem. Soc.* 108:2093–94, 1986) were run on a Bruker AF-500 MHz NMR (Bruker Analytical, Karlsruhe, Germany). A one dimensional 13C-NMR and a DEPT (distortionless enhancement through polarization transfer; Doddrell et al., *J. Mag. Reson.* 48:323, 1982) were also run on this instrument. A $^{13}$C-$^{13}$C INADEQUATE (Mareci and Freeman, *J. Mag. Reson.* 48:158–63, 1982) was run on 180 mg of this compound in 650 μl of DMSO-$d_6$ on a Varian Unity-Plus 500 MHz NMR (Varian Associates, Palo Alto, Calif.).

D. Physicochemical Characterization of 1494A

The dried acetonitrile-soluble organic material was then redissolved into 10 ml of acetonitrile. One ml of this preparation was filtered though a 0.45 μm nylon filter and injected onto a preparatory HPLC column (22×250 mm, 10 μm, 300 Å, Vydac™ (Hewlett Packard, Wilmington, Del.)). The HPLC column was eluted using a gradient of 50% acetonitrile in water to 100% acetonitrile in 60 min with a flow rate of 20 ml/min. UV detection was employed using a dual wavelength detector set at 220 and 270 nm. Fractions were collected every minute by an automatic fraction collector, and 0.5 ml of each of these fractions was removed and evaporated to dryness. The dried fractions were redissolved in DMSO for bioassay. The activity correlated with a pure peak that eluted at 21.5 min using the system mentioned above. From four preparative HPLC runs, 12.6 mg of this compound was accumulated for structure elucidation.

To minimize degradation of the active compound, solvents other than acetonitrile or DMSO should be avoided. In addition, any hint of acidity (such as would occur if an HPLC column had previously been exposed to trifluoroacetic acid) should also be assiduously avoided.

1494A a) Apparent Molecular Formula: $C_{32}H_{43}N_1O_4$ b) Molecular Weight: (FABMS,3NBA) $(M+H)^+$= M/Z 506 HRMS calcd. for $C_{32}H_{44}N_1O_4$=506.3252 HRMS obsd. for $C_{32}H_{44}N_1O_4$=506.3270 c) Specific rotation: $[\alpha]_D^{25}$= d) Ultraviolet Absorption spectra: λmax nm ε ETOH= e) Infrared Absorption Spectra: (KBr pellet) 3375, 2952, 2920, 2866, 1722, 1700, 1650, 1613, 1597, 1516, 1451, 1375, 1223, 1108, 1054, 848, 832, 680, 625 cm$^{-1}$;

f) $^1$H Nuclear Magnetic Resonance Spectrum: (Bruker WM-500, DMSO-$d_6$ as solvent and reference) 9.115 (1H,s), 8.557 (1H, s), 7.489 (1H,s), 6.991 (2H, d, J=8.0 Hz), 6.567 (2H, d, J=8.5 Hz), 6.061 (1H,s), 5.287 (1H, s), 4.443 (1H, d, J=8.5 Hz), 3.493 (1H, dd, J=12.0, 7.0 Hz), 3.011 (1H, d, J=13.0 Hz), 2.882 (1H, d, J=13.5 Hz), 2.734 (1H, d, J=7 Hz), 1.990 (1H, m), 1.643 (1H, ?), 1.636 (1H, ?), 1.596 (1H, 48), 1.427 (3H, s), 1.411 (1H, dd?, J=?, 7.5 Hz), 1.398 (2H, ?), 1.251 (3H, s), 1.184 (1H, dq ?, J=7.0, 5.5 Hz ), 1.045 ( 1H, dq ?, J=7.5 5.0 Hz ), 0.846 (3H, s), 0.804 (?H, ?), 0.803 (3H, d, J=5.5 Hz), 0.791 (1H, ?), 0.722 (3H, dd, J=7.5, 7.0 Hz), 0.645 (3H, d, J=6.5 Hz);

g) $^{13}$C- Nuclear Magnetic Resonance Spectrum: (Bruker WM-500, DMSO-$d_6$ as solvent and reference) 196.61 (C=O), 167.23 (C=O), 156.12 (ch), 155.99 (q), 135.62 (q), 135.56 (ch), 135.45 (ch), 132.00 (q), 131.29 (ch), 131.29 (ch), 129.80 (q), 125.30 (q), 114.50 (ch), 114.50 (ch), 86.03 (q), 50.56 (ch), 48.45 (ch), 48.00 (ch2), 42.73 (ch2), 39.31 (ch), 35.54 (ch2), 35.08 (q), 33.52 (ch), 29.76 (ch2), 26.87 (ch), 23.20 (ch2), 22.72 (ch3), 21.91 (ch3), 20.34 (ch3), 20.23 (ch3), 14.43 (ch3), 11.98 (ch3).

A summary of NMR experimental data regarding compound 1494 is presented in Table 1, below.

TABLE 1

Summary of NMR experiments - 1494

| Assignment | $^{13}$C-(δ, ppm) DMSO-$d_6$ | $^1$H-(δ, ppm) DMSO-$d_6$ | $^1$H—$^{13}$C (HMBC) | $^{13}$C—$^{13}$C (INADEQUATE) |
|---|---|---|---|---|
| N(1)—H | | 8.557 | | |
| C(2) | 167.23 | | N(1)—H | C(3) |
| C(3) | 135.60 | | N(1)—H | |
| C(4) | 156.12 | 7.489 | N(1)—H | C(5) |
| C(5)—OH | 86.03 | 6.061 | N(1)—H, H(4), H(6a), H(6b) | C(4), C(6) |
| C(6)—H$_2$ | 42.73 | 3.011, 2.882 | C(5)—OH | C(5), C(7) |
| C(7) | 125.30 | | C(10)—OH, H(6a), H(6b), H(8, 12), H(9, 11) | C(8, 12) |
| C(8)—H/C(12)—H | 131.29 | 6.991 | H(9, 11) | C(9, 11) |
| C(9)—H/C(11)—H | 114.50 | 6.567 | H(8, 12) | C(8, 12), C(10) |
| C(10)—OH | 155.99 | 9.115 | H(9, 11), H(8, 12) | C(9, 11) |
| C(13) | 196.61 | | H(4), H(14) | |
| C(14)—H | 48.45 | 3.493 | H(15) | C(15), C(22) |
| C(15)—H | 50.56 | 2.734 | H(31), H(30), H(17) | C(14), C(16), C(24) |
| C(16) | 129.80 | | | C(15), C(17) |
| C(17)—H | 135.45 | 5.287 | H(15), H(32) | C(16), C(23) |
| C(18)—H | 48.00 | 1.411, 0.791 | H(32) | C(19), C(23) |
| C(19)—H | 26.87 | 1.643 | H(33) | C(18), C(20), C(33) |
| C(20)—H$_2$ | 35.54 | 0.804, 1.636 | | C(19), C(21) |
| C(21)—H$_2$ | 23.20 | 1.398 | | C(20) |
| C(22)—H | 39.31 | 1.596 | H(32), H(15) | |
| C(23) | 35.08 | | H(14) | |
| C(24) | 132.00 | -- | H(30), H(15) | C(15) |
| C(25)—H | 135.56 | 4.443 | H(30), H(29) | |
| C(26)—H | 33.52 | 1.99 | H(29), H(28) | C(27), C(29) |
| C(27)—H$_2$ | 29.76 | 1.045, 1.184 | H(29), H(28) | C(26), C(28) |
| C(28)—H$_3$ | 11.98 | 0.722 | | C(27) |
| C(29)—H$_3$ | 20.23 | 0.645 | | C(26) |
| C(30)—H$_3$ | 14.4 | 1.251 | | |
| C(31)—H$_3$ | 21.91 | 1.427 | | C(16) |
| C(32)—H$_3$ | 20.34 | 0.846 | | C(23) |
| C(33)—H$_3$ | 22.72 | 0.803 | | C(19) |

11

The structure of 1494 is depicted below:

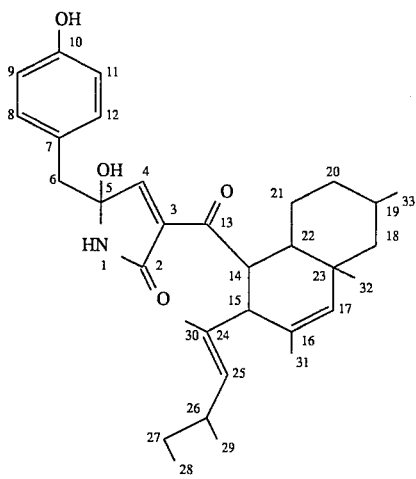

Example 2

Isolation and Characterization of 2158

A. Fermentation Procedure:

Three ml of a mycelial suspension of MO2158 were used to inoculate a 250 ml baffled shake flask containing 100 ml of SKPX medium (potato flour, 75 g/l; soy flakes, 40 g/l; $Na_2HPO_4 \cdot 12\ H_2O$, 9.0 g/l; $KH_2PO_4$, 1.5 g/l; Ban 800 MG, 0,075 g/l; Pluronic 100%, 0.1 ml/l). The culture was incubated for 13 d at 26° C. at 200 RPM rotation. Alternatively, MO2158 was cultured in a one liter fermentation using SKPX medium.

B. Extraction Procedure:

The entire culture (medium plus cells) was was extracted with ethyl acetate, as described for 1494 in Example 1.B, above, except that the pH was not adjusted to 9.0 prior to extraction.

C. Physicochemical Characterization of 2158:

A fraction of the dried ethyl acetate crude material (260 mg) was separated between 100 ml methanol/water (9:1), and 100 ml n-heptane. The methanol/water phase was further purified by reverse phase HPLC on a C18 column (Dupont, 120 Å, 10 μM, OdDMeSi material, 250×20 mm), eluted with 70% acetonitrile at a flow rate of 9 ml/min, and UV detected at 225 nm. Briefly, 210 mg of material was dissolved in 7.5 ml acetonitrile and injected onto the column (3 similar runs). Fractions were collected every 13.5 ml, and the total amount of 2158 collected from these HPLC fractionations was approximately 33 mg.

2158A a) Apparent Molecular Formula: $C_{33}H_{45}N_1O_4$
b) Molecular Weight: (EI-MS) $(M)^+$=m/z 519 HRMS calcd. for $C_{33}H_{45}N_1O_4$=HRMS obsd. for $C_{33}H_{45}N_1O_4$=519.3378
c) Specific rotation: $[\alpha]_D^{25}$=
d) Ultraviolet Absorption spectra:
e) Infrared Absorption Spectra:
f) $^1$H Nuclear Magnetic Resonance Spectrum: (Bruker 300 MHz, $CDCl_3$ as solvent and reference) 7.48 (1H, d, J=1.4 Hz), 7.09 (2H, d, J=8.5 Hz), 6.76 (2H, d, J=8.4 Hz), 6.20 (1H, bs), 5.32 (1H, s), 5.2 (1H, bs), 4.70 (1H, d, J=9.4 Hz), 3.86 (1H, dd J=7.9, 12.5 Hz), 3.15 (1H, d, J=14 Hz), 3.00 (1H, d, J=14 Hz), 3.00 (1H, d, J=7.0 Hz), 2.35 (1H, bs), 2.16 (1H, m), 1.77 (1H, m), 1.75 (1H, dd, J=10.4, 12.4 Hz), 1.60 (1H, m), 1.55 (1H,m), 1.48 (3H, bs), 1.46 (1H, m), 1.44 (3H, bs), 1.27 (1H,m), 1.11 (1H, m), 1.00 (1H, t, J=12.5 Hz ), 0.91 (3H, bs), 0.85 (3H, d, J=6.4 Hz), 0.81 (3H, d, J=6.6 Hz), 0.80 (3H, t, J=7.3 Hz), 0.80 (1H, m), 0.52 (3H, d, J=6.5 Hz);
p1 g) $^1$H Nuclear Magnetic Resonance Spectrum (Bruker 300 MHz, DMSO-$d_6$ as solvent and reference) 9.09 (1H, bs), 8.60 (1H, bs), 7.45 (1H, d), 6.97 (2H, d), 6.55 (2H, d), 6.10 (1H, bs), 5.27 (1H, s), 4.50 (1H, d), 3.72 (1H, dd), 3.05 (1H, d), 2.90 (1H, d), 2.72 (1H, d), 2.02 (1H, m), 1.75 (1H, m), 1.55 (1H, m), 1.5 (1H, m), 1.5 (1H, m), 1.45 (3H, s), 1.4 (1H, m), 1.32 (3H, s), 1.25 (1H, m), 1.09 (1H, m), 0.87 (3H, s), 0.8 (1H, m), 0.8 (1H, m), 0.80 (3H, d), 0.75 (3H, t), 0.70 (3H, d), 0.35 (3H, d);

h) 13C- Nuclear Magnetic Resonance Spectrum: (Bruker 300 MHz, $CDCl_3$ as solvent and reference) 196.5 (q), 167.9 (q), 155.4 (ch), 155.0 (q), 136.0 (ch), 136.0 (ch), 136.0 (q), 135.1(q), 131.5 (ch), 131.5 (ch), 128.7 (q), 125.7 (q), 115.6 (ch), 115.6 (ch), 85.8 (q), 50.8 (ch), 48.6 (ch2), 48.2 (ch) , 46.7 (ch2) , 45.5 (ch), 43.0 (ch2), 36.3 (q), 34.1 (ch), 32.7 (ch), 30.3 (ch2), 27.5 (ch), 24.8 (ch3) , 22.6 (ch3) , 22.4 (ch3), 22.0 (ch3) , 21.0 (ch3), 14.0 (ch3), 12.5 (ch3).

The structure of 2158 is depicted below:

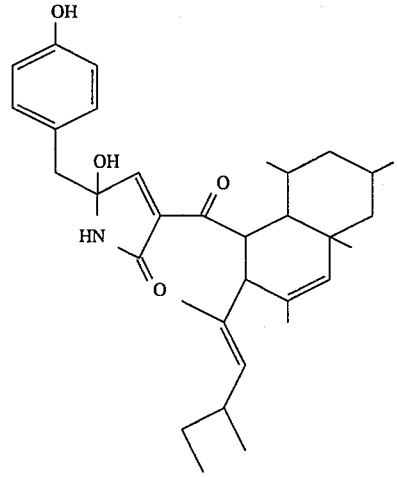

Example 3

Biological Activity of 1494

The remodeling pathway of PAF synthesis is the pathway involved in pathological processes, such as inflammation, and particularly in neutrophil-mediated processes. The de novo pathway of PAF synthesis is required for normal physiological functions. Therefore, a desirable, anti-inflammatory, therapeutically effective PAF modulator will down-regulate the remodeling pathway, but will have little or no effect on the de novo pathway of PAF synthesis.

Briefly, to assay the remodeling pathway acetyl-transferase, 400 ml of 500 mg/ml bovine serum albumin (fatty acid free; Sigma) in PBS (120 mM NaCl, 2.7 mM KCl, 10 mM phosphate buffer, pH 7.4, supplemented with 10 μM $CaCl_2$) was added to each well of a 96-well, flat-bottom microtiter plate. The plate was incubated for 15 min at ambient temperature, then the wells were aspirated and 50 μl of PBS was added to each well. Duplicate or triplicate test samples in DMSO (≦5% (v/v)) were added to each well.

HL-60 cells (a stable, transformed hematopoietic cell line) were combined with PBS containing 0.05% TWEEN-20 and mixed vigorously at 500 rpm for 30 sec. This treatment permeabilized the HL-60 cells. An aliquot (50 μl)

of HL-60 lysate so formed was added to each well of the plate, and the plate was incubated for 5 min at ambient temperature with gentle shaking.

PAF acetyl-transferase substrates were added to each well, such that 25 µl of the following solution was added per well: Lyso-PAF (160 mM; Calbiochem, La Jolla, Calif.), acetyl-CoA (80–400 mM; Calbiochem), and $^3$H-acetyl-CoA (25 µCi/ml; Amersham). The plate was gently mixed for 45 sec and then incubated at 37° C. for 20 min.

Newly synthesized PAF was extracted by adding 1.25 mg of AMBERCHROM CG-71 resin (Supelco, Bellefonte, Pa.) in 25 µl of distilled water to each well. The plate was gently shaken for 1 min, following which the resin was collected on a 102 mm×258 mm glass-fiber filter using a MICRO-CELL HARVESTER (Skatron, Waltham, Mass.). The filter was washed with 500 ml water to remove unincorporated $^3$H-acetyl-CoA. Following the wash, the filter was dried in a microwave oven for 5–10 min.

After the filter was dried, it was soaked in 10 ml of Beta Plate scintillation fluid (LKB, Loughborough, England), and bound counts were determined in a TOP COUNT scintillation counter (Pharmacia). Percentage inhibition was determined by dividing the average of 2 or 3 replicate wells by the average of 3 control wells (5% DMSO alone), and multiplying by 100.

The de novo pathway of PAF synthesis was assayed in the same manner, except: (1) PBS buffer was supplemented with 5 mM EGTA, rather than 10 µM $CaCl_2$; and (2) newly synthesized 1-O-alkyl-2-sn-acetyl-3-glycerophosphate, rather than newly synthesized PAF, was extracted with AMBERCHROM CG-71 resin.

Compound 1494 was tested for inhibition of remodeling PAF-acetyltransferase at a variety of concentrations (0.1 to 25 µg/well). A dose-dependent inhibition ranging from about 12% (0.1 µg/well) to about 71% (8.3 µg/well) was observed. At 25 µg/well of 1494, about 65% inhibition was detected.

Compound 1494 was tested for inhibition of de novo PAF-acetyltransferase at the same concentrations as above (i.e., 0.1 to 25 µg/well). At 0.1 to 8.3 µg/well, no significant inhibition of de novo PAF-acetyltransferase was observed. These results demonstrate that Compound 1494 is a selective modulator of the remodeling pathway of PAF synthesis.

Compound 2158 was similarly tested for inhibition of remodeling and de novo PAF-acetyltransferase at the same concentrations as above (i.e., 0.1 to 25 µg/well). No significant inhibition of de novo PAF-acetyltransferase was observed at any of these concentrations. Inhibition of remodeling PAF-acetyltransferase ranged from 59% inhibition at 25 µg/well to 0% inhibition at 0.9 to 0.1 µg/well.

Compound 1494 was assayed for a variety of inhibitory activities. For testing, compound 1494 was placed in 0.5% DMSO (with partial solubility), at concentrations of 0.01, 0.1, 1 and 10 µM. Compound 1494 exhibited significant displacement of [$^3$H]PAF from PAF binding sites ($IC_{50}$ of about 3 µM), indicative of functional receptor antagonism. Displacement of [$^3$H]pyrilamine from histamine $H_1$ binding sites ($IC_{50}$ of about 3 µM) was noted, but may be unrelated to functional receptor agonism or antagonism. Displacement of [3H]dexamethasone from glucocorticoid binding sites ($IC_{50}$ of about 3 µM) was also observed. Inhibition of the following activities was also detected:

$IC_{50} \approx 3$ µM:
EGF tyrosine kinase
P56$^{lck}$ tyrosine kinase
P59$^{fyn}$ tyrosine kinase IC50≈10 µM: 5-lipoxygenase IC50≈100 µM: Phospholipase $A_2$ IC50≈300 µM: Cyclooxygenase In contrast to the above listed inhibitory activities, compound 1494 stimulated B cell proliferation in the presence of LPS, and T cell proliferation in the presence of ConA.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the structure:

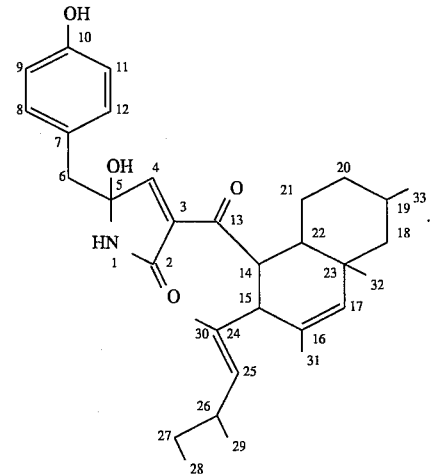

2. A compound having the structure:

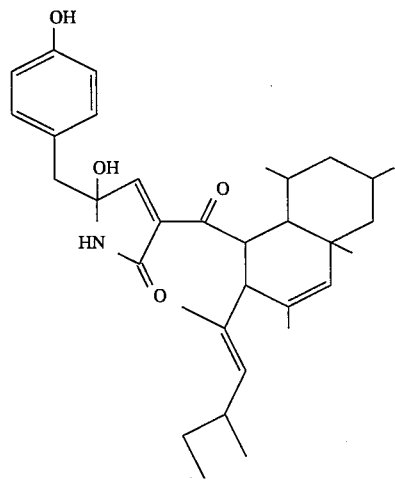

3. A pharmaceutical composition comprising the compound of claim 1 or the compound of claim 2 in combination with a pharmaceutically acceptable vehicle.

4. The pharmaceutical composition of claim 3 further comprising an anti-inflammatory agent selected from the group consisting of a steroidal anti-inflammatory drug and a non-steroidal anti-inflammatory drug.

5. A method for reducing inflammation in a mammal comprising administering to said mammal a therapeutically effective amount of the pharmaceutical composition of claim 3.

6. The method of claim 5 further comprising the step of administering to the recipient an anti-inflammatory agent selected from the group consisting of a steroidal anti-inflammatory drug and a non-steroidal anti-inflammatory drug.

7. The method of claim 6, wherein the anti-inflammatory agent is administered before, after or concurrent with administration of the pharmaceutical composition of claim 3.

8. The method of claim 5, wherein the mammal has a medical indication selected from the group consisting of septic shock, anaphylaxis, thrombosis, adult respiratory syndrome, ischemia-reperfusion, necrotizing enterocolitis, asthma, rheumatoid arthritis, an autoimmune disease and an acquired immunoregulatory abnormality.

* * * * *